(12) United States Patent
Ricketts

(10) Patent No.: US 7,775,212 B2
(45) Date of Patent: Aug. 17, 2010

(54) DISPOSABLE, SELF-OPENING BODILY FLUID BARRIER

(76) Inventor: Robert A. Ricketts, P.O. Box 1, Polson, MT (US) 69860

( * ) Notice: Subject to any disclaimer, the term of this patent is extended or adjusted under 35 U.S.C. 154(b) by 0 days.

(21) Appl. No.: 12/023,257

(22) Filed: Jan. 31, 2008

(65) Prior Publication Data
US 2008/0210245 A1      Sep. 4, 2008

Related U.S. Application Data

(60) Provisional application No. 60/888,109, filed on Feb. 5, 2007.

(51) Int. Cl.
*A61F 5/37* (2006.01)
(52) U.S. Cl. .................................................. 128/849

(58) Field of Classification Search ......... 128/849–856; 602/13
See application file for complete search history.

(56) References Cited

U.S. PATENT DOCUMENTS 3,986,505 A * 10/1976 Power ........................ 128/846
5,699,568 A * 12/1997 Couldridge .................... 5/628

* cited by examiner

*Primary Examiner*—Kim M Lewis
(74) *Attorney, Agent, or Firm*—Wood, Herron & Evans L.L.P.

(57) ABSTRACT

Shown is a disposable, self-opening bodily fluid barrier formed of a sheet of impermeable material. The device may include a main body panel, side panels, and a foot panel to fully wrap and encase an injured or diseased patient and contain any bodily fluids released from the patient. The device may also include fluid expansion chambers such that, when filled with a pressurized gas, will cause the device to fully open into position for use without assistance.

1 Claim, 5 Drawing Sheets

DISPOSABLE, SELF-OPENING BODILY FLUID BARRIER

RELATED APPLICATION

This application claims priority based on my U.S. Provisional Patent Application Ser. No. 60/888,109 entitled DISPOSABLE, SELF-OPENING BODILY FLUID BARRIER filed Feb. 5, 2007.

TECHNICAL FIELD

This invention relates generally to a bodily fluid barrier for use by emergency or rescue personnel to contain potentially hazardous body fluids and liquid waste released by a patient. More specifically, it relates to a disposable, self-opening wrap on which a patient may be placed, followed by folding over of side and bottom flaps, in order to contain such fluids and prevent contamination of rescue personnel, equipment, or the surrounding environment.

BACKGROUND OF THE INVENTION

It is commonly recognized that the release of body fluids which may harbor bacteria, viruses, or other hazardous and toxic agents by patients being transported or rescued by emergency response personnel presents potentially serious dangers. Additionally, because all such spilled bodily fluids must be treated as potentially infectious, any contaminated equipment, including vehicles, must be cleaned prior to use on or with another patient in order to reduce or eliminate the risk of cross contamination or infection.

In some cases, the required cleaning can be both costly and burdensome due to the time when the equipment must be removed from use. For example, when the interior of an air rescue helicopter becomes contaminated with a large volume of a patient's bodily fluid, it must be removed from service and many parts of the interior cabin may need to be disassembled in order to gain access to and clean every crevice into which fluid may have seeped. This process is very costly and requires that a multi-million dollar rescue vehicle, for which there may be no available substitute, be taken out of service for several days.

Liquid impermeable and/or absorbent sheets have been described in the prior art and used for such purposes. One example is shown in U.S. Pat. No. 5,135,792 titled DISPOSABLE, SELF-ENVELOPING AND SELF-CONTAINING ON-DEMAND, SUPER ABSORBENT COMPOSITE, issued Aug. 4, 1992. Other proposed solutions are shown in U.S. Pat. No. 5,615,425 titled FITTED SHEET FOR USE AS A DISPOSABLE STRETCHER/GURNEY LINEN, issued Apr. 1, 1997 and U.S. Pat. No. 6,453,492 titled SHEET FOR STRETCHER/GURNEY, issued Sep. 24, 2002.

Large sheets or drapes can be very cumbersome to use, difficult to position and keep in place on a stretcher or gurney, and equally difficult to open from a folded condition by a single person. The present invention addresses each of these concerns.

SUMMARY OF THE INVENTION

The present invention provides a disposable, self-opening bodily fluid barrier in the form of an impermeable sheet of material that will fully wrap or encase an injured or diseased patient. The device may include a main body panel of substantially rectangular shape having a length and width slightly greater than that of a typical adult patient. Laterally extending from longitudinal sides of the main body panel are flaps or side panels which can be folded up and over the patient in an overlapping fashion. A foot panel may also extend outwardly from a foot end of the main panel to allow closure of the bottom end to prevent escape of bodily fluids.

An inner surface of the sheet material may be covered with an absorbent material. Also, the device may be provided with a means for inflating chambers coextensive with the sheet of impermeable material so that it may be rapidly and automatically deployed from a folded and rolled condition.

Other features, aspects and objects of the present invention will be apparent from the various figures of the drawing and written description of a preferred embodiment which, together with any later-appended claims, make up the entire disclosure of the present invention.

BRIEF DESCRIPTION OF THE DRAWING

Like reference numerals are used to indicate like parts throughout the various figures of the drawing, wherein.

DETAILED DESCRIPTION OF THE INVENTION

Figure 1:
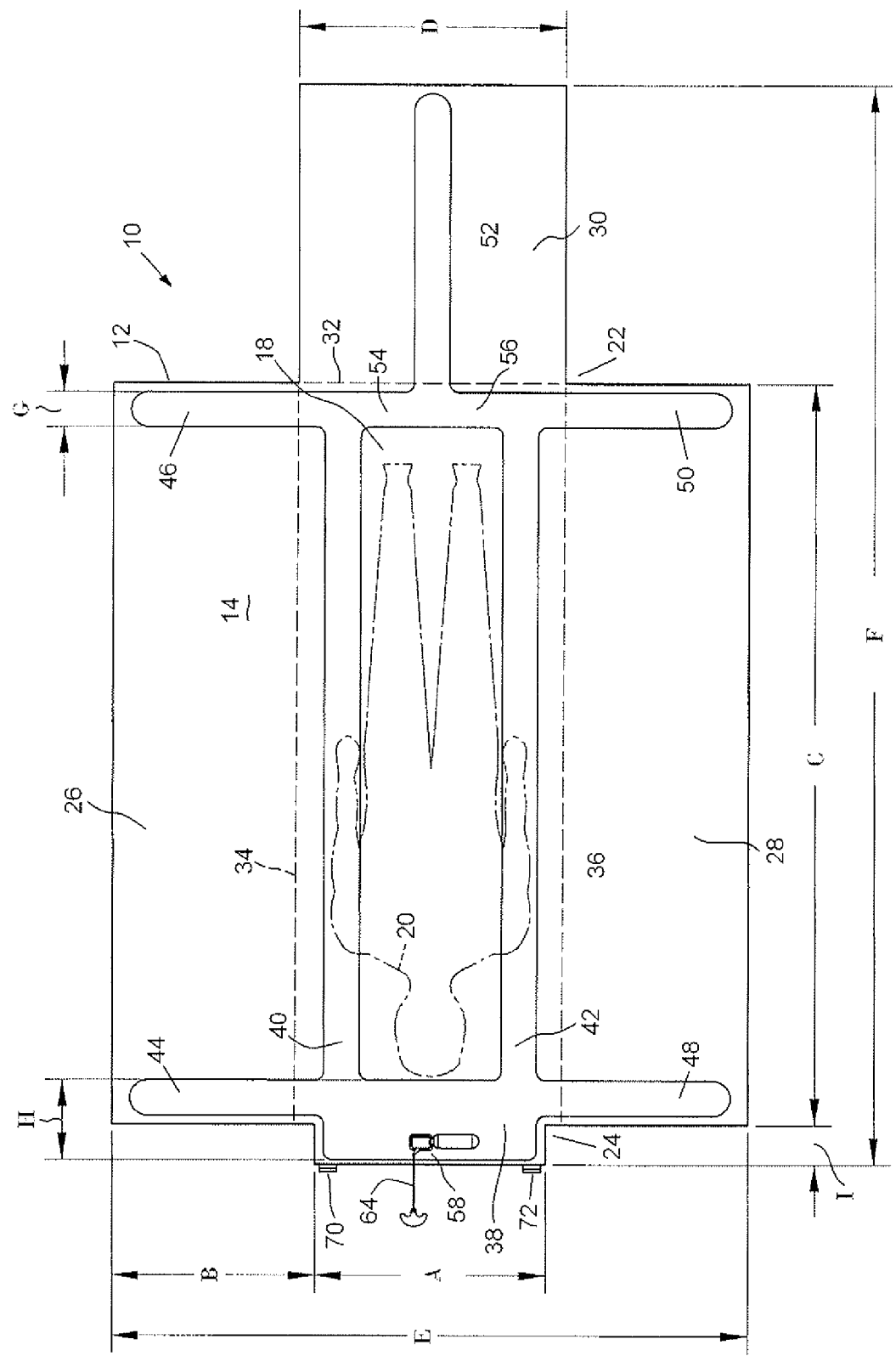
FIG. 1 shows a top plan view of a preferred embodiment of the present invention in a fully deployed position.

Referring to the various figures of the drawing, and first to FIG. 1 therein is shown at 10 an embodiment of the present invention which incorporates certain preferred features. In preferred form, the disposable, self-opening bodily fluid barrier device 10 is formed from a sheet 12 of impermeable material, such as plastic or a plastic coated fabric. The overall body of the device 10 may be formed from a single main sheet of material or from multiple pieces joined together with impermeable seams. The sheet of material 12 has inner and outer surfaces 14, 16. If desired, the inner surface 14 may be covered with a layer of absorbent material or, in the case of the entire sheet 12 being made of an absorbent material, the impermeable barrier layer is applied to the outer surface 16.

The sheet 12 comprises a main body section 18 which is substantially rectangular and is sized and shaped to be slightly longer and wider than a typical person (shown in phantom lines at 20). The main panel 18 includes a foot end 22 and a head end 24. Laterally adjacent side edges of the main panel 18 are left and right flaps or panels 26, 28 which are substantially equal in length and width to the main body panel 18. Extending from the foot end 22 may be a foot flap 30 having dimensions which are generally as wide as or slightly wider than that of the main panel 18 and a length generally at least equal to that of its width.

Referring again to FIG. 1, approximate dimensions of a preferred embodiment may be as follows: A=26" (66 cm); B=23" (58.5 cm); C=84" (213 cm); D=30" (76 cm); E=72" (183 cm.); F=122.5" (311 cm); G=4" (10 cm); and H=9" (23 cm).

In use, the device 10 is situated with the main body portion 18 positioned over a stretcher, litter, gurney, or bed upon which the injured or diseased patient 20 is to be placed. Side panels 26, 28 and foot panel 30 would extend beyond the boundaries of the stretcher, litter, gurney or bed and would hang downwardly by gravity to the extent that the main body portion 18 is raised above floor or ground level. After the patient 20 is so situated, the foot panel 30 is folded upwardly over the foot and lower legs of the patient 20 and side panels 26, 28 are folded over one another in order to wrap or envelope the patient completely. Of course, head end portions of the side panels 26, 28 would be folded away to expose the head of a living patient 20.

Figure 2:
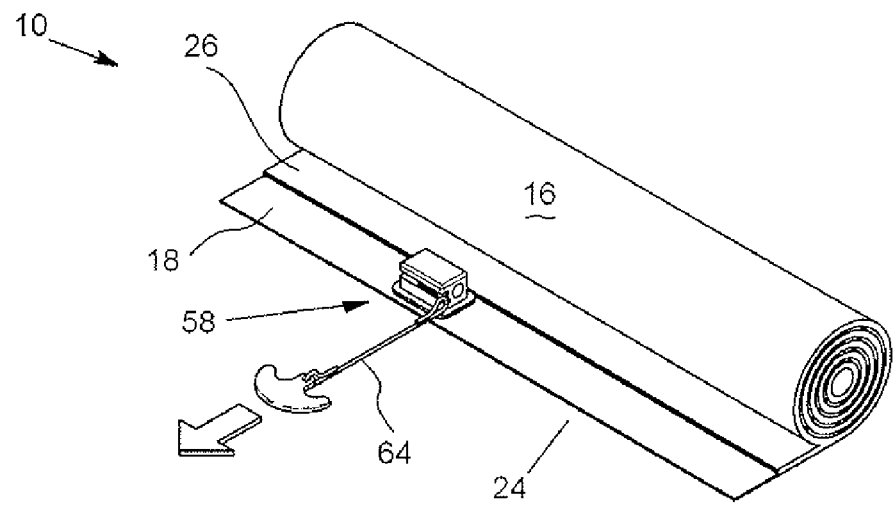
FIG. 2 shows a pictorial view of the device in a stowed condition.

For storage prior to use, it is expected that the device 10 would be packed as follows. From a flat and open position, substantially as shown in FIG. 1, the foot panel 30 is folded upwardly substantially along line 32. Left and right side panels 26, 28 would be folded over the main body panel 18 (overlapping one another) substantially along lines 34 and 36. Thereafter, the now superimposed panels 18, 26, 28, 30 would be rolled form the foot end 22 toward the head end 24. The resulting packed device 10 would now appear substantially as shown in FIG. 2. Hook and loop fasteners or other devices (not shown) could be used to keep the device 10 in the packed condition until ready for use.

According to another important aspect of the invention, the device 10 is self-opening or self-deploying substantially as shown in the sequence illustrated in FIGS. 2-5. This may be accomplished such as by inflating interconnected fluid air chambers formed integrally with or on the impermeable sheet of material 12.

Figure 4:
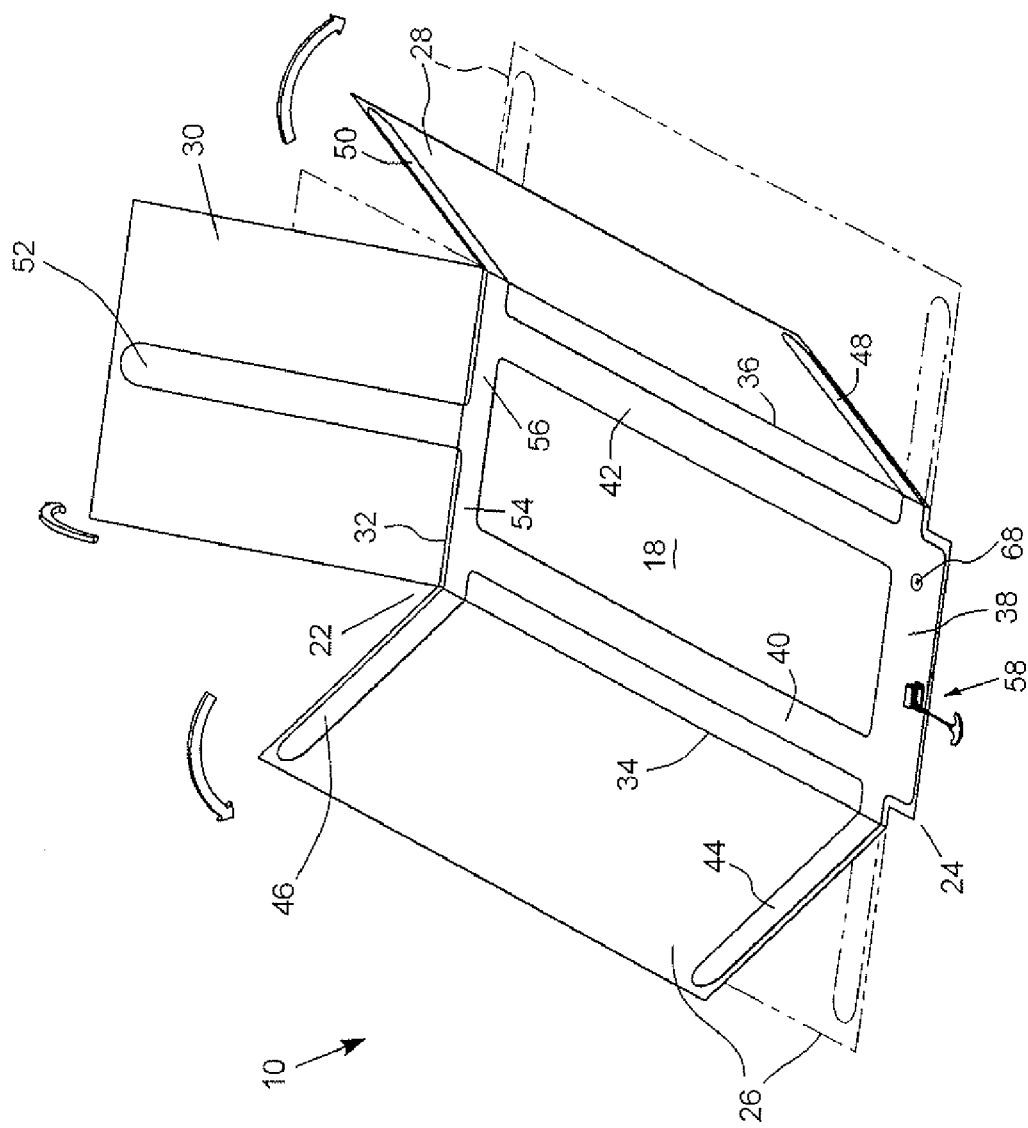
FIG. 4 shows the device in a further deployed position.
Figure 5:
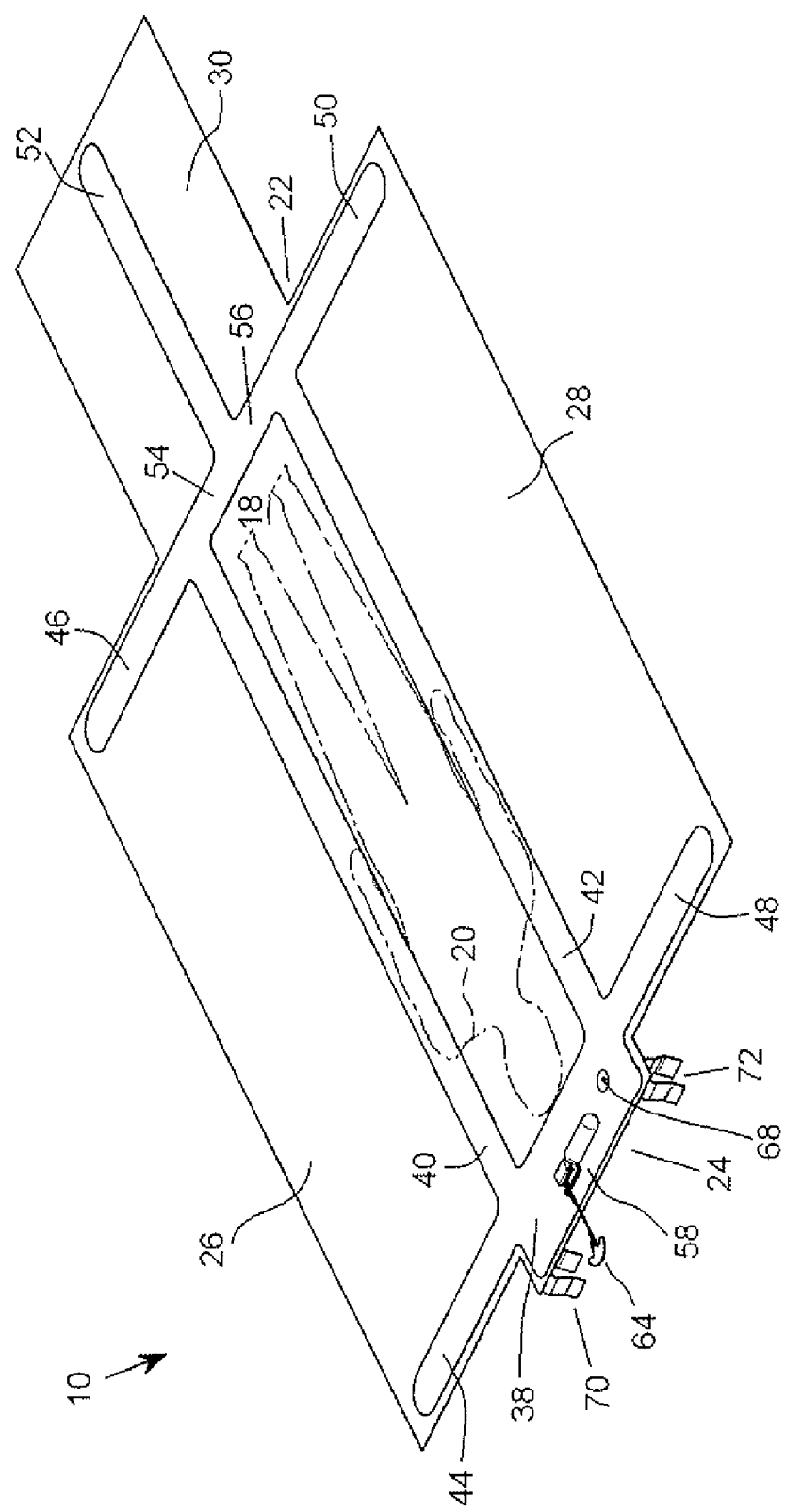
FIG. 5 shows the device in a fully deployed position.

Referring now in particular to FIGS. 1, 4 and 5, therein is shown a series of inflatable chambers or channels formed by welding, gluing or otherwise sealing a second layer of impermeable material to the first sheet of impermeable material 12. These chambers or channels may be applied to either the inner surface 14 or outer surface 16 of the impermeable sheet of material 12. If applied to the inner surface 14, the exposed surface of the chambers or channels may or may not be covered with an absorbent material. These chambers may include a head chamber 38, a pair of laterally spaced apart main body chambers 40, 42 extending substantially the full length of the main body panel 18, laterally extending side panel chambers 44, 46, 48, 50, and one or more foot panel chamber 52 operably connected to the main chambers 40, 42 by connecting chambers 54, 56.

Figure 6:
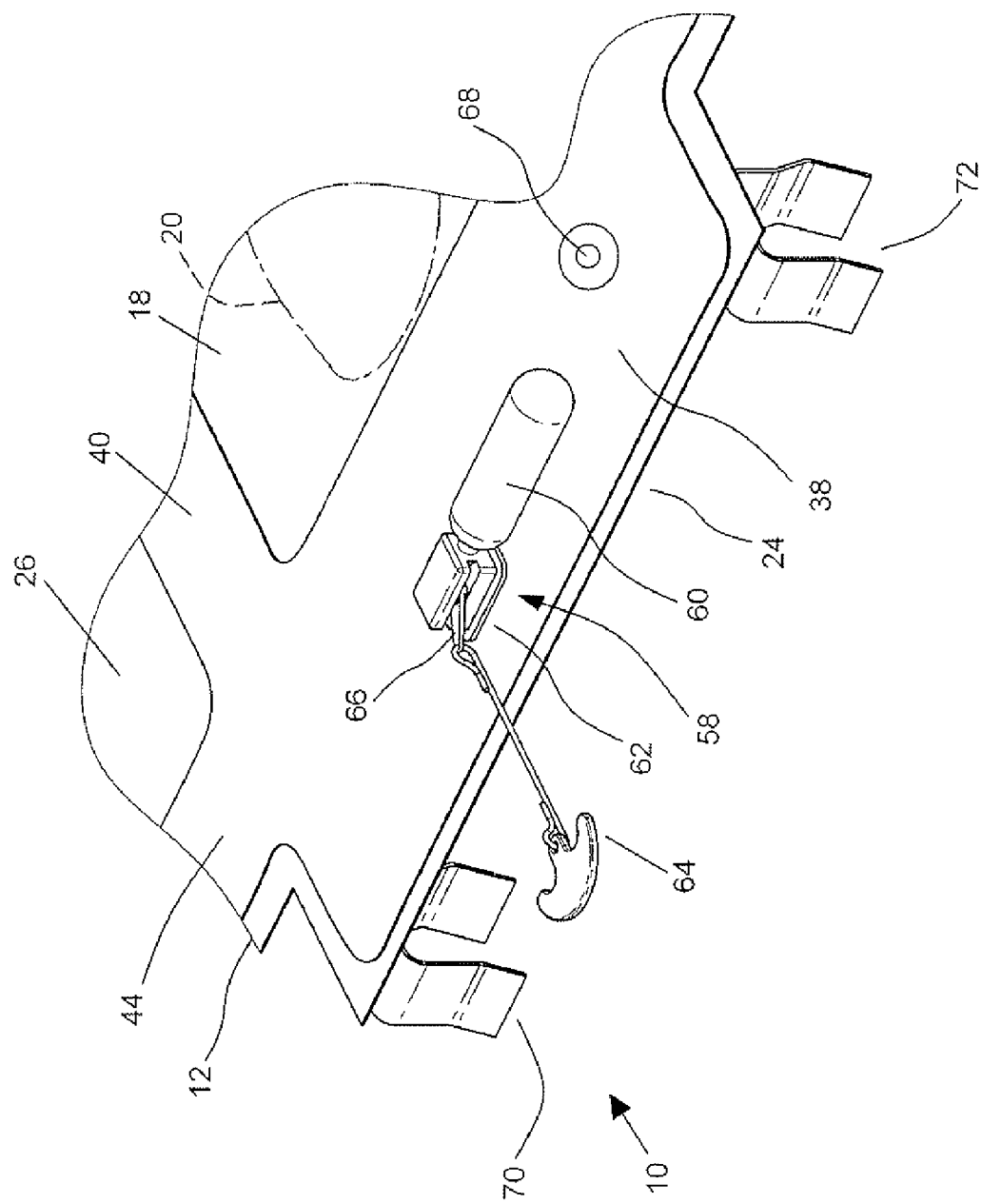
FIG. 6 shows a detail view of the attachment and inflation devices.

As shown in more detail in FIG. 6, an inflation device 58 of ordinary construction is preferably located at or near the head end 24. Inflation devices of this general type have been known and in use for decades in self-inflating life vests and rafts. Typically the inflation device 58 includes a small cylinder 60 of compressed gas (such as $CO_2$) and a valve 62. The valve 62 may be operated in any common manner, such as by a pull string or handle 64 attached to a valve lever 66, the movement of which either opens a valve or pierces an end closure of the cylinder 60 to allow the compressed gas to rapidly escape and expand to fill the chambers 38, 40, 42, 44, 46, 48, 50, 52, 54, 56. It is expected that the cylinder would contain more than enough compressed fluid to fill and overfill all of the chambers. For this reason, and because an eventual complete depressurization of the chambers is desirable, a pressure relief valve 68 of well-known construction is provided in fluid communication with the chambers, such as in the head chamber 38. Additionally, or alternatively, pressure relief openings may be provided at distal ends of each of the side chambers 44, 46, 48, 50 and foot panel chamber 52. Although the device may be manufactured inexpensively enough that the entire device 10 may be disposed of after use, it may also be reused after proper cleaning, replacement of the cylinder 60 of compressed gas, and re-packing into condition for proper re-deployment.

Figure 3:
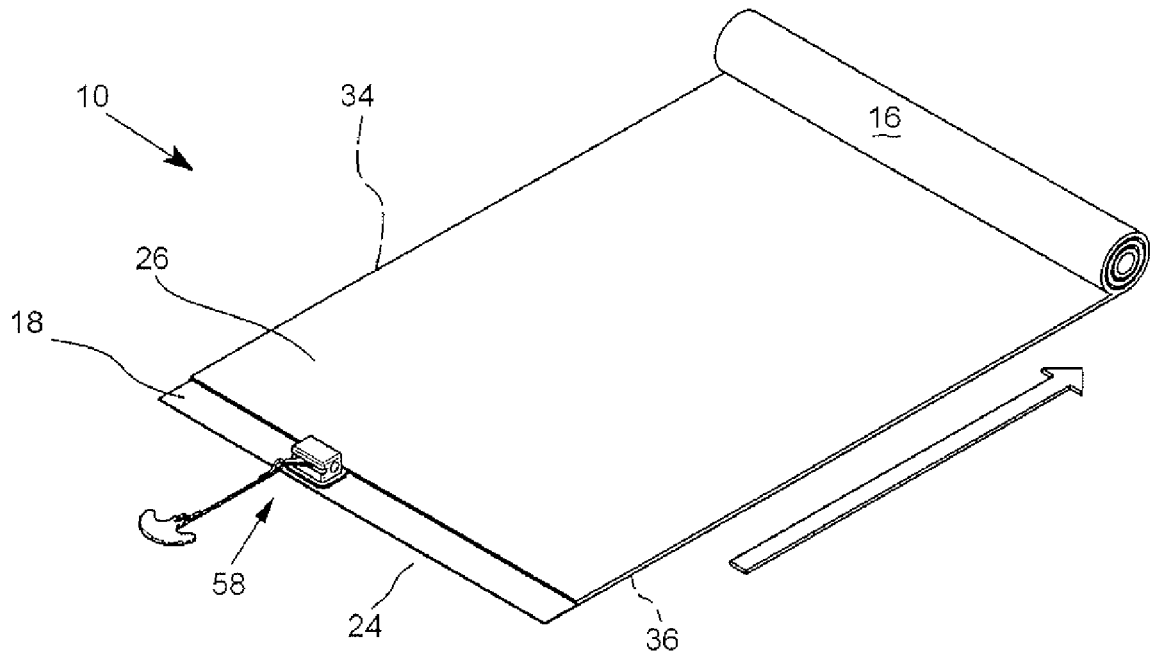
FIG. 3 shows the device of FIG. 2 in a partially deployed position.

Referring now again to FIG. 6, attachment devices 70, 72, such as straps with hook and loop closure devices at the ends (not shown), may be included, preferably at the head end 24 to attach the device 10 to a stretcher, litter, gurney or bed prior and during deployment. With the device 10 in a packed condition (FIG. 1) and secured in place, it may be deployed by releasing the compressed gas in the cylinder 60 such as by pulling on the handle 64 to actuate the valve 62. Doing so causes the compressed gas to expand first into the head end chamber 38 and then into main body chambers 40, 42. This will cause the device 10 to begin to unroll (as shown in FIG. 3) as the main body chambers 40, 42 become turgid from the pressurized gas expanding in the chambers. Once the previously packed device 10 is completely unrolled, the side panels 26, 28 and foot panel 30 will unfold and be extended as the pressurized gas expands into and fills the side panel chambers 44, 46, 48, 50 and foot panel chamber 52, as shown in FIG. 4.

Fully opening and positioning the device 10 can be accomplished in a matter of seconds by a single person using only one hand. Accordingly, the device 10 will be quickly opened and in place, ready for a patient 20 to be placed thereon, as shown in FIG. 5. It is important that, once the device 10 is fully unfolded, all pressure within the expansion chambers be completely released so that at least the side panel chambers 44, 46, 48, 50 and foot panel chamber 52 are flaccid. This allows the foot panel 30 to be folded upwardly over the patients feet and lower legs, followed by the side panels 26, 28 being folded upwardly and over the patient 20 to quickly and completely wrap the patient 20 in an impermeable sheet, open only at the head end 24, to completely contain, and if desired, absorb any bodily fluids released from the patient 20 so as to prevent contamination of rescue workers, equipment, and the surrounding environment from contamination.

It can readily be seen that there are numerous benefits that result from employing the concepts of the present invention. The foregoing description of a preferred embodiment of the present invention has been presented for purposes of illustration and description. It is not intended to be exhaustive or to limit the invention to the precise form disclosed. Obvious modifications or variations are possible in light of the above teachings. For example, variations in the overall shape of the sheet of material 12, particularly the side panels 26, 27 and foot panel 30, may be used depending upon the particular need to be filled. Additionally, expansion chambers of a wide variety of shapes, sizes and positions may be utilized in order to allow deployment of the device at a selected rate or sequence. Furthermore, constrictions may be employed at the proximal ends of the side panel expansion chambers 44, 48 which are at the head end 24 of the device 10 in order to delay expansion of those chambers 44, 48 until the device 10 is fully unrolled.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by any allowed claims when interrupted in accordance with the breadth to which they are fairly, legally and equitably entitled. The drawings and preferred embodiments do not and are not intended to limit the ordinary meaning of the claims and their fair and broad interpretation in any way.

What is claimed is:

1. A self-opening bodily fluid barrier for a patient, comprising:

a substantially impermeable sheet of material comprising a substantially rectangular main body panel having a predetermined length and width with first and second opposite ends and first and second opposite side edges, first and second side panels substantially coextensive with the side edges of the main body panel and having a width substantially equal to the width of the main body panel, a foot panel substantially coextensive with the second end of the main body panel and extending away from the main body panel a length generally at least equal to that of its width;

a series of elongated inflatable chambers in fluid connection with one another on the sheet of material comprising at least one chamber positioned to extend substantially the entire length of the main body panel, first and second longitudinally spaced apart and laterally extending side chambers on each of the side panels, and a longitudinally extending chamber on the foot panel;

an inflation device comprising a container of compressed inflation gas containing enough gas to, when released, more than fill the series of inflatable chambers, a main valve operably interconnecting the container and the series of chambers near the first end of the main body portion and a relief valve operably connected with the series of chambers to vent inflation gas from the chambers when the internal pressure reaches a predetermined point sufficient to fully extend the main body, side and foot panels by turgid inflation of the chambers, wherein, when the bodily fluid barrier has a packed condition in which the first and second side panels are folded onto the main body panel along the side edges, the foot panel is folded onto the main body panel at the second end, and the entire folded sheet is rolled from the second end toward the first end and a deployed condition in which all panels are fully extended and unfolded from the main body panel, the bodily fluid barrier being transitioned from the packed condition to the deployed condition by operation of the main valve to release compressed gas from the container into the series of chambers, the chambers being substantially filled with the gas to extend the chambers to a turgid condition and operation of the relief valve to vent the gas after deployment.

\* \* \* \* \*